(12) United States Patent
Balicki et al.

(10) Patent No.: US 9,814,392 B2
(45) Date of Patent: Nov. 14, 2017

(54) VISUAL TRACKING AND ANNOTATON OF CLINICALLY IMPORTANT ANATOMICAL LANDMARKS FOR SURGICAL INTERVENTIONS

(75) Inventors: Marcin A. Balicki, Baltimore, MD (US); Russell H. Taylor, Severna Park, MD (US); Gregory D. Hager, Baltimore, MD (US); Peter L. Gehlbach, Hunt Valley, MD (US); James T. Handa, Baltimore, MD (US); Rajesh Kumar, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/505,058

(22) PCT Filed: Nov. 1, 2010

(86) PCT No.: PCT/US2010/054988
§ 371 (c)(1),
(2), (4) Date: Apr. 30, 2012

(87) PCT Pub. No.: WO2011/053921
PCT Pub. Date: May 5, 2011

(65) Prior Publication Data
US 2012/0226150 A1    Sep. 6, 2012

Related U.S. Application Data

(60) Provisional application No. 61/256,531, filed on Oct. 30, 2009.

(51) Int. Cl.
*A61B 5/00* (2006.01)
*A61B 3/10* (2006.01)
(Continued)

(52) U.S. Cl.
CPC ............ *A61B 5/0066* (2013.01); *A61B 3/102* (2013.01); *A61B 3/1225* (2013.01); *A61B 3/13* (2013.01);
(Continued)

(58) Field of Classification Search
None
See application file for complete search history.

(56) References Cited

U.S. PATENT DOCUMENTS 5,554,155 A * 9/1996 Awh et al. ................ 606/16
6,167,296 A * 12/2000 Shahidi .................... 600/427
(Continued)

FOREIGN PATENT DOCUMENTS

CN          1802626 A      7/2006
CN        101222882 B      3/2013
(Continued)

OTHER PUBLICATIONS

International Search Report and Written Opinion for PCT/US2010/054988.
(Continued)

*Primary Examiner* — Long V Le
*Assistant Examiner* — Angela M Hoffa
(74) *Attorney, Agent, or Firm* — Venable LLP

(57) ABSTRACT

A visual tracking and annotation system for surgical intervention includes an image acquisition and display system arranged to obtain image streams of a surgical region of interest and of a surgical instrument proximate the surgical region of interest and to display acquired images to a user; a tracking system configured to track the surgical instrument relative to the surgical region of interest; a data storage system in communication with the image acquisition and display system and the tracking system; and a data processing system in communication with the data storage system, (Continued)

the image acquisition and display system and the tracking system. The data processing system is configured to annotate images displayed to the user in response to an input signal from the user.

23 Claims, 7 Drawing Sheets

(51) Int. Cl.

| | | |
|---|---|---|
| A61B 34/20 | (2016.01) | |
| A61B 3/12 | (2006.01) | |
| A61B 8/08 | (2006.01) | |
| A61B 3/13 | (2006.01) | |
| A61B 90/00 | (2016.01) | |
| A61B 5/06 | (2006.01) | |
| A61B 5/107 | (2006.01) | |
| G06F 17/24 | (2006.01) | |
| A61F 9/007 | (2006.01) | |
| G02B 21/00 | (2006.01) | |

(52) U.S. Cl.
CPC ............ *A61B 5/0084* (2013.01); *A61B 5/061* (2013.01); *A61B 5/1076* (2013.01); *A61B 5/743* (2013.01); *A61B 5/7475* (2013.01); *A61B 8/5261* (2013.01); *A61B 90/37* (2016.02); *G06F 17/241* (2013.01); *A61B 2034/2065* (2016.02); *A61B 2090/3614* (2016.02); *A61B 2090/3735* (2016.02); *A61B 2560/0295* (2013.01); *A61F 9/007* (2013.01); *G02B 21/0012* (2013.01)

(56) References Cited

U.S. PATENT DOCUMENTS

| | | | | |
|---|---|---|---|---|
| 6,428,553 | B1* | 8/2002 | Trese | 606/161 |
| 6,975,898 | B2* | 12/2005 | Seibel | 600/473 |
| 7,126,303 | B2* | 10/2006 | Farritor et al. | 318/568.12 |
| 7,831,294 | B2* | 11/2010 | Viswanathan | 600/425 |
| 8,073,528 | B2* | 12/2011 | Zhao et al. | 600/424 |
| 8,108,072 | B2 | 1/2012 | Zhao et al. | |
| 8,147,503 | B2* | 4/2012 | Zhao et al. | 606/130 |
| 8,398,541 | B2* | 3/2013 | DiMaio et al. | 600/111 |
| 8,401,616 | B2* | 3/2013 | Verard et al. | 600/424 |
| 8,423,120 | B2* | 4/2013 | Tynes et al. | 600/424 |
| 8,528,566 | B2* | 9/2013 | Loesel et al. | 128/898 |
| 8,554,307 | B2* | 10/2013 | Razzaque et al. | 600/424 |
| 2002/0171669 | A1 | 11/2002 | Meron et al. | |
| 2004/0097805 | A1* | 5/2004 | Verard | A61B 1/00071 600/428 |
| 2004/0254454 | A1* | 12/2004 | Kockro | A61B 19/52 600/424 |
| 2005/0015005 | A1 | 1/2005 | Kockro | |
| 2005/0027199 | A1* | 2/2005 | Clarke | 600/473 |
| 2005/0182295 | A1* | 8/2005 | Soper et al. | 600/117 |
| 2005/0200324 | A1 | 9/2005 | Guthart et al. | |
| 2006/0100505 | A1* | 5/2006 | Viswanathan | 600/424 |
| 2006/0174065 | A1* | 8/2006 | Kuzara et al. | 711/123 |
| 2006/0258938 | A1 | 11/2006 | Hoffman et al. | |
| 2007/0021738 | A1* | 1/2007 | Hasser et al. | 606/1 |
| 2007/0115481 | A1 | 5/2007 | Toth et al. | |
| 2007/0167702 | A1 | 7/2007 | Hasser et al. | |
| 2007/0238981 | A1 | 10/2007 | Zhu et al. | |
| 2007/0276195 | A1 | 11/2007 | Xu et al. | |
| 2007/0276226 | A1* | 11/2007 | Tal | 600/424 |
| 2008/0004603 | A1 | 1/2008 | Larkin et al. | |
| 2008/0033240 | A1 | 2/2008 | Hoffman et al. | |
| 2008/0039705 | A1 | 2/2008 | Viswanathan | |
| 2008/0062429 | A1 | 3/2008 | Liang et al. | |
| 2008/0119725 | A1* | 5/2008 | Lloyd | 600/424 |
| 2008/0177256 | A1 | 7/2008 | Loesel et al. | |
| 2008/0287783 | A1 | 11/2008 | Anderson | |
| 2009/0036902 | A1 | 2/2009 | DiMaio et al. | |
| 2009/0220125 | A1 | 9/2009 | Ren et al. | |
| 2010/0168763 | A1 | 7/2010 | Zhao et al. | |
| 2010/0228123 | A1* | 9/2010 | Brennan et al. | 600/437 |
| 2010/0249506 | A1 | 9/2010 | Prisco | |
| 2011/0105898 | A1 | 5/2011 | Guthart et al. | |
| 2011/0106102 | A1* | 5/2011 | Balicki et al. | 606/130 |
| 2011/0122365 | A1* | 5/2011 | Kraus et al. | 351/206 |
| 2012/0130258 | A1* | 5/2012 | Taylor et al. | 600/476 |

FOREIGN PATENT DOCUMENTS

| | | |
|---|---|---|
| EP | 2075763 A1 | 7/2009 |
| JP | 2002-510230 A | 4/2002 |
| JP | 2008-006169 A | 1/2008 |

OTHER PUBLICATIONS

Leven et al., DaVinci Canas: A Telerobotic Surgical System with Integrated, Robot-Assisted, Laparoscopic Ultrasound Capability, Proceedings of MICCAI 2005.

Su et al., Augmented reality during robot-assisted laparoscopic partial nephrectomy: Toward real-time 3d-ct to stereoscopic video registration, Journal of Urology, 2009.

Official Notice of Rejection dated Sep. 2, 2014 in Japanese Patent Application No. 2012-537171.

* cited by examiner

VISUAL TRACKING AND ANNOTATON OF CLINICALLY IMPORTANT ANATOMICAL LANDMARKS FOR SURGICAL INTERVENTIONS

CROSS-REFERENCE OF RELATED APPLICATION

This application claims priority to U.S. Provisional Application No. 61/256,531 filed Oct. 30, 2009, the entire contents of which are hereby incorporated by reference, and is a U.S. national stage application under 35 U.S.C. & 371 of PCT/US2010/054988 filed Nov. 1, 2010, the entire contents of which are incorporated herein by reference.

This invention was made with Government support of Grant No. 1R01 EB 007969-01, awarded by the Department of Health and Human Services, NIH; and Grant No. EEC-9731478, awarded by the NSF. The U.S. Government has certain-rights in this invention.

BACKGROUND

1. Field of Invention

The field of the currently claimed embodiments of this invention relates to systems and methods of acquiring and displaying information during surgical procedures, and more particularly to systems and methods of acquiring and displaying information that include visual tracking of surgical instruments and annotation of information displayed.

2. Discussion of Related Art

Currently surgeons use a number of intraoperative diagnostic and surgical and/or treatment devices for operating on small tissue regions, e.g., laparoscopic ultrasound and/or RF ablation devices. The surgeon observes the device's position relative to the anatomy through a video feed. In the case of diagnostic instruments, the surgeon has to note this position and the imaging results and track this location with the anatomy over time. Over time, the surgeon may want to revisit particular anatomy for an intervention or inspection. If the surgeon does not recall or is not sure about the location or the content of a prior diagnostic image associated with a particular area, the diagnostic device might have to be reintroduced to the operating field, which is time consuming. In the case of surgical devices, the surgeon has to map the already treated area relative to some visible landmarks. This is difficult when the treatment is inside the target tissue, or does not alter the tissue's appearance. Missed, over treated or incorrect treatment locations are to be avoided. The surgeon may choose to inspect or treat a number of anatomical regions, which could be sparsely located, e.g. 10 landmarks. This adds to cognitive load on the surgeon in an already challenging minimally invasive procedure. Furthermore, the anatomy may deform, or change color naturally, or from the intervention itself, which adds to the difficulty of tracking the relevant landmarks and associated intraoperative information.

In the case of vitroretinal surgery, for example, it has been very rare to interrogate the retina with intraocular imaging probes. However, with the discovery of new real time intraoperative imaging modalities (GRIN lens endoscopes, spectroscopy, ultrasound, optical coherence tomography (OCT)), compatible probes and multifunction instruments, new surgical techniques may be possible. These new technologies image tissue at very close distances and very small volumes. The resulting data is sparsely located, requiring the surgeon to track multiple scans or images with the corresponding anatomical locations in the microscope view, which adds significant cognitive load to the already challenging surgical task. This can become more difficult with altered anatomy due to surgical manipulation, bleeding, bio-markers, swelling as well as inherent changes in the field of view, lighting methods and/or directions and intraocular fluid conditions.

There thus remains the need for improved visual tracking and annotation systems and methods for surgical intervention.

SUMMARY

A visual tracking and annotation system for surgical intervention according to some embodiments of the current invention has an image acquisition and display system arranged to obtain image streams of a surgical region of interest and of a surgical instrument proximate the surgical region of interest and to display acquired images to a user; a tracking system configured to track the surgical instrument relative to the surgical region of interest; a data storage system in communication with the image acquisition and display system and the tracking system; and a data processing system in communication with the data storage system, the image acquisition and display system and the tracking system. The data processing system is configured to annotate images displayed to the user in response to an input signal from the user.

A visual tracking and annotation method for surgical intervention according to some embodiments of the current invention includes acquiring an image of a surgical region of interest and of a surgical instrument proximate the surgical region of interest, tracking the surgical instrument relative to the surgical region of interest, and displaying the surgical region of interest and the surgical instrument. The displaying includes annotations added in response to an input signal from the user.

A computer-readable medium according to some embodiments of the current invention includes non-transient storage of software for visual tracking and annotation for surgical intervention, which when executed by a computer system, include processing image data of a surgical region of interest and of a surgical instrument proximate the surgical region of interest to provide an image of the surgical region of interest and of the surgical instrument; processing the image data to track the surgical instrument relative to the surgical region of interest; processing the image data and an input signal from a user to annotate the image; and displaying the image of the surgical region of interest and the surgical instrument with the annotations.

BRIEF DESCRIPTION OF THE DRAWINGS

Further objectives and advantages will become apparent from a consideration of the description, drawings, and examples.

DETAILED DESCRIPTION

Figure 1:
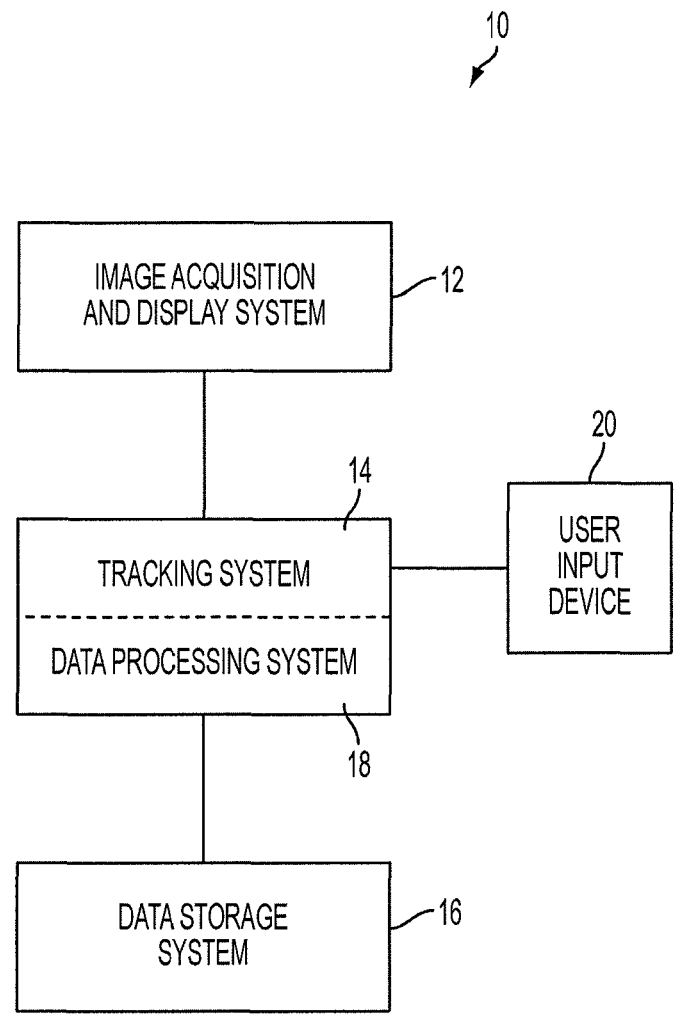
FIG. 1 is a schematic illustration of a visual tracking and annotation system for surgical intervention according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of the current invention are directed to systems and methods for displaying surgically relevant data collected intraoperatively as a video augmented with overlay annotation. The intraoperative imaging and/or treatment information can be registered to corresponding anatomical landmark locations in intraoperative video, and tracked and visualized in various representations over time in the video. In addition, external tool tracking systems and/or robots could also be included according to some embodiments of the current invention. In that case, they may need to be registered to the video system. The system according to some embodiments of the current invention can be used with any instrument visible in the surgical video field of view. In a simple case, the instrument can be a pointing device, used to paint a region of interest which is then tracked in subsequent video (telestration). In more complex cases, the instruments can be any intra-operative diagnostic and/or imaging devices, such as ultrasound, spectroscopy probes, oxygenation sensors, optical coherence tomography, confocal microscopy, endoscopes, GRIN endoscopes, nerve function measurement, autoflourescene or interventional treatment devices, such as RF liver ablation lasers, electric stimulation, cryoablation, etc. The information from these devices can be linked to the location where it was collected, or in the case of treatment, where it was applied. The information can be displayed as a picture-in-picture in the same screen as the real time surgical video feed or on a separate screen, for example.

The individual annotation can be added to the set or removed by the surgeon. The annotations can have a number of states depending on their temporal nature, whether their associated anatomy is visible (occlusion from tools), deformation by the procedure, or a natural change by a certain amount. These states can be represented in color, intensity, visibility, or textual annotation. The annotations themselves can be in a form of a point, line, a region, a volume, a textual annotation, an image corresponding to the shape of the instrument, or the shape of the imaging area or volume. These annotations can create inherent relationships, whether special or contextual based on landmarks, tissue types (underlying properties of the tissue being interrogated or treated from the intraoperative imaging itself), or device type. Information from multiple devices can be annotated on the same video in some embodiments of the current invention.

Some embodiments of the current invention can include user interfaces, such as pedals, computer mices, touch screens, voice recognition input, or it can be linked to sensor activity level on instruments being used. In some embodiments, gesture recognition of the instrument in the video can be included. Furthermore, tool position tracking in the video can allow the system to provide richer information from simple sensors according to an embodiment of the current invention. An embodiment of the current invention can include intraoperative OCT in which the system creates a B-Scan image from A-Scans and corresponding pose estimation from a video tool tracking module. Further embodiments can extend such an approach to a volumetric C-Scan like information representation, for example.

Some aspects of the current invention include, but are not limited to the following:

1. Annotations are acquired relative to anatomy across image streams (video). We annotate the position on the anatomy (i.e. organ) with sensor stream data.

2. "Information fusion": Sensor data is time series data that can be correlated over a video or spatially tracked pose sequence relative to the anatomy. The sensor position moving over a region of interest can be tracked and this time synchronized tool position can be combined with tool sensor data stream to create an image over video sequence. For example, an A-Scan stream transformed into B-Scan and/or M-scan data.

3. Reviewing of annotations can involve the user interacting with annotations. Simple interactions can involve selecting "active" annotation by pointing at it with the tracked tool, or other input (voice, pedal etc). More complex interactions may indicate where the instrument is in the annotation itself.

4. Sensor streams can be correlated over multiple video image sequences.

FIG. 1 provides a schematic illustration of a visual tracking and annotation system 10 for surgical intervention according to an embodiment of the current invention. The visual tracking and annotation system 10 includes an image acquisition and display system 12 arranged to obtain image streams of a surgical region of interest and of a surgical instrument proximate the surgical region of interest and to display acquired images to a user. The image acquisition and display system 12 can include optical components, such as, but not limited to a surgical microscope, and endoscope and/or a video camera, for example. The image acquisition and display system 12 can also include one or more displays, such as, but not limited to, video displays or head mounted displays. The visual tracking and annotation system 10 also includes a tracking system 14 configured to track the surgical instrument relative to the surgical region of interest, a data storage system 16 in communication with the image acquisition and display system 12 and the tracking system 14, and a data processing system 18 in communication with the data storage system 16, the image display system 12 and the tracking system 14. The data processing system 18 can include the processors of one or more personal computers, for example, which can be local, clustered and/or distributed, as desired for the particular application. The tracking system 14 can be implemented on a computer in some embodiments of the current invention and can use conventionally available image recognition and tracking algorithms. In some embodiments, the tracking system could be implemented on the data processing system 18, or it could be a separate system in other embodiments. The data storage system 16 can be selected from one or more of a wide range of available data storage devices according to the particular application. The data processing system 18 is configured to annotate images displayed to the user in response to an input signal from the user.

The visual tracking and annotation system 10 can also include a user input device 20 that is in communication with the data processing system to provide the input signal according to some embodiments of the current invention. The input device 20 can be, but is not limited to, one or more pedals, keypads, switches, microphones, eye tracking systems or surgical instruments, according to some embodiments of the current invention.

Figure 2:
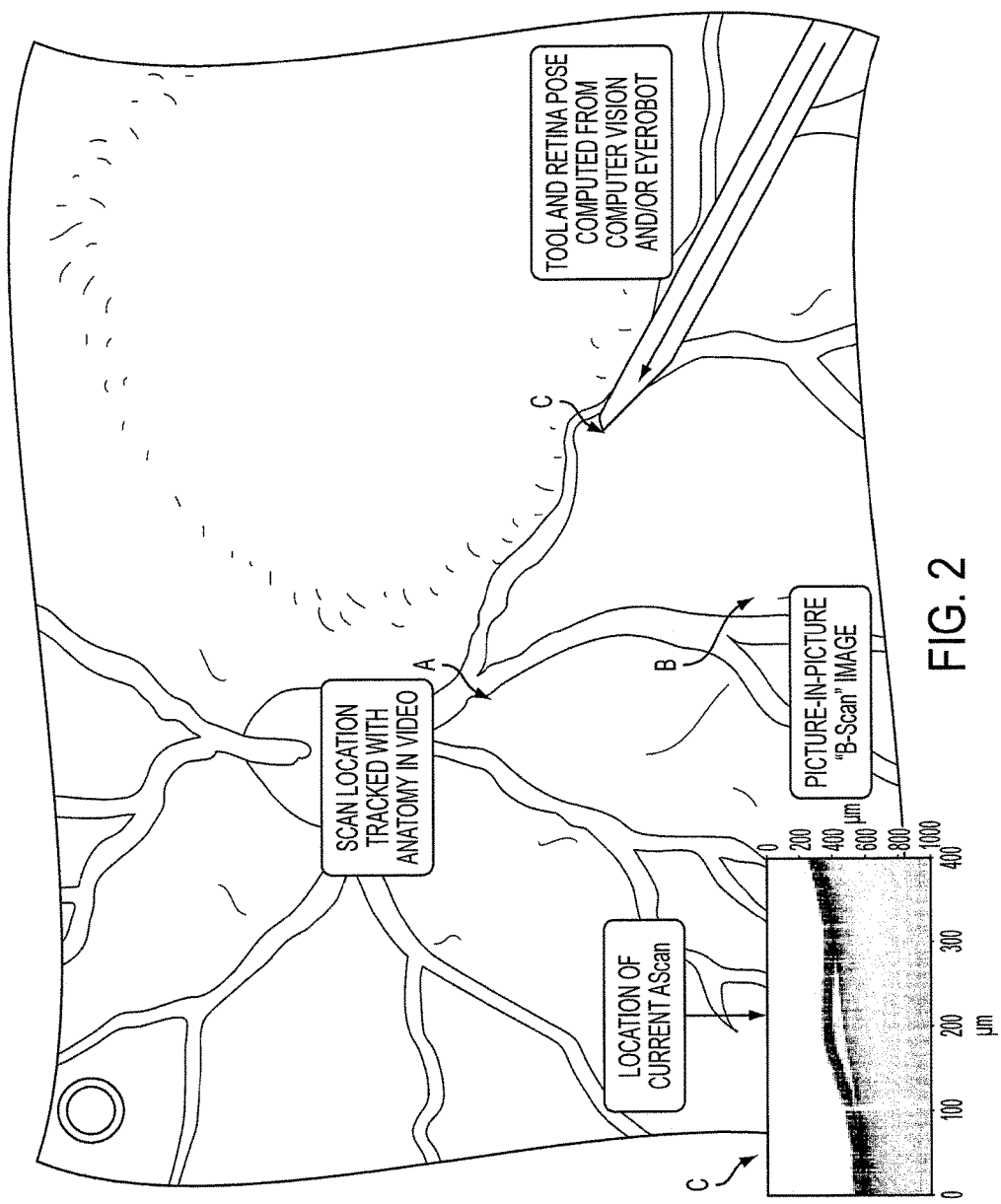
FIG. 2 shows an example of a displayed image for a visual tracking and annotation system for surgical intervention according to an embodiment of the current invention.

In some embodiments of the current invention, the data processing system 18 can be configured to annotate images displayed to the user to include at least one of a position or a track of the surgical instrument. FIG. 2 shows an example of an image annotated with three OCT paths labeled A, B and C according to an embodiment of the current invention. FIG. 2 also shows a picture-in-picture of OCT M-mode data displayed in response to the user's placement of the surgical instrument. This is only one example of the wide range of possible annotations that could be included in various embodiments of the current invention. The broad concepts of the current invention are not limited to this particular example. In some embodiments, the data processing system 18 can be configured to annotate images displayed to the user to display information from the data storage system that corresponds to a position of the surgical instrument. For example, the M-mode data in FIG. 2 was captured by a scan with an OCT device and recalled from data storage system 16 to be displayed when the OCT device was placed over the path that had been previously scanned.

In some embodiments of the current invention, the user input device 20 can be a surgical instrument that is suitable to be tracked by the tracking system. The surgical instrument can include a sensor system constructed and arranged to provide a data stream regarding localized portions of the surgical region of interest and can be in communication with the data storage system such that data obtained by the surgical instrument can be saved for later retrieval. In some embodiments of the current invention, the sensor system can include at least one of an optical sensor system, an ultrasound sensor system, or force-sensing system.

Surgical instruments according to some embodiments of the current invention can allow for simultaneous imaging and surgical intervention functionality integrated into a single instrument. Registration of the instrument to the optical sensor can be achieved by a reference portion of the instrument that is visible in the field of view of the optical sensor according to an embodiment of the current invention. Furthermore, multiple imaging probes can be integrated into the instrument for increased imaging volume, multiple imaging directions, increased resolution, or to provide other types of imaging for simultaneous multimodal imaging functionality according to other embodiments of the current invention. Multiple imaging point probes (multi core fiber, or multifiber bundle) can improve the registration of the tool tip to optical sensor in some embodiments.

Figure 3:
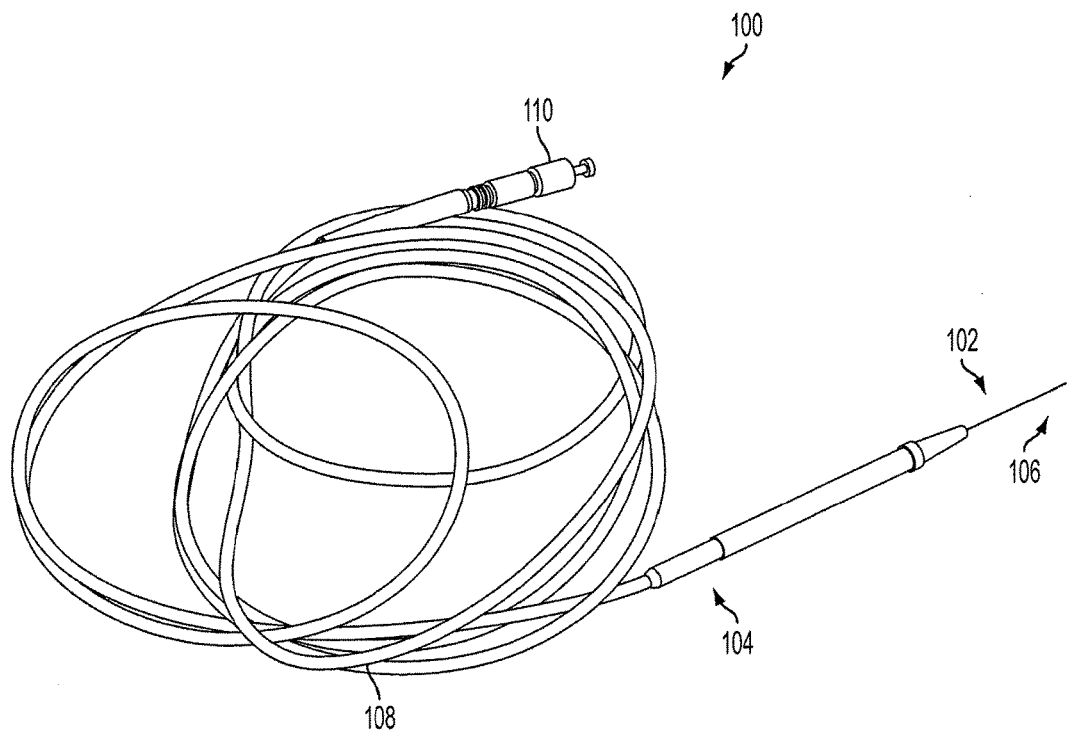
FIG. 3 shows an embodiment of a surgical instrument according to an embodiment of the current invention.

A surgical instrument 100 according to an embodiment of the current invention is shown in FIG. 3. Such a surgical instrument can be used as a user input device 20 according to some embodiments of the current invention. The surgical instrument 100 includes a surgical tool 102 having a proximal end 104 and a distal end 106, and an optical sensor having at least a portion attached to the surgical tool 102. In FIG. 3, an optical fiber that is not directly visible runs along a lumen within the surgical tool 102 and is attached to the surgical tool 102. The optical fiber is enclosed within a protective cable 108, which has a standard fiber coupler 110 in this example. As one can see more clearly in FIG. 4, the surgical tool 102 has a portion that is suitable to provide a reference portion 112 of the surgical tool 102. The optical sensor 114 (see FIG. 5) has an end 116 fixed relative to the reference portion 112 of the surgical tool 102 such that the reference portion 112 of the surgical tool 102 can be detected along with tissue 118 that is proximate or in contact with the distal end 106 of the surgical tool 102 while in use.

Figure 4:
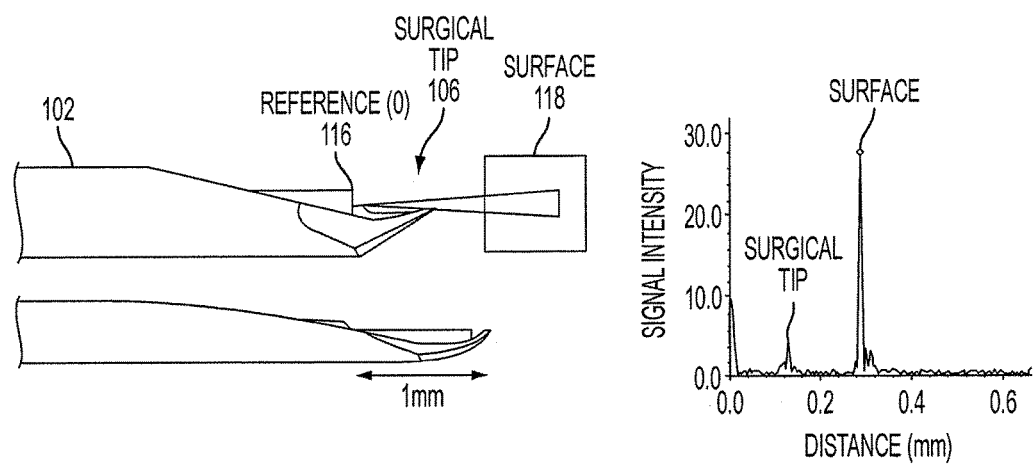
FIG. 4 shows a CAD side view of microsurgical pick with integrated fiber optic OCT probe according to an embodiment of the current invention (Top Left); a photograph of an actual prototype (Bottom Left); and A-Scan data of a sample using the prototype (Right).
Figure 5:
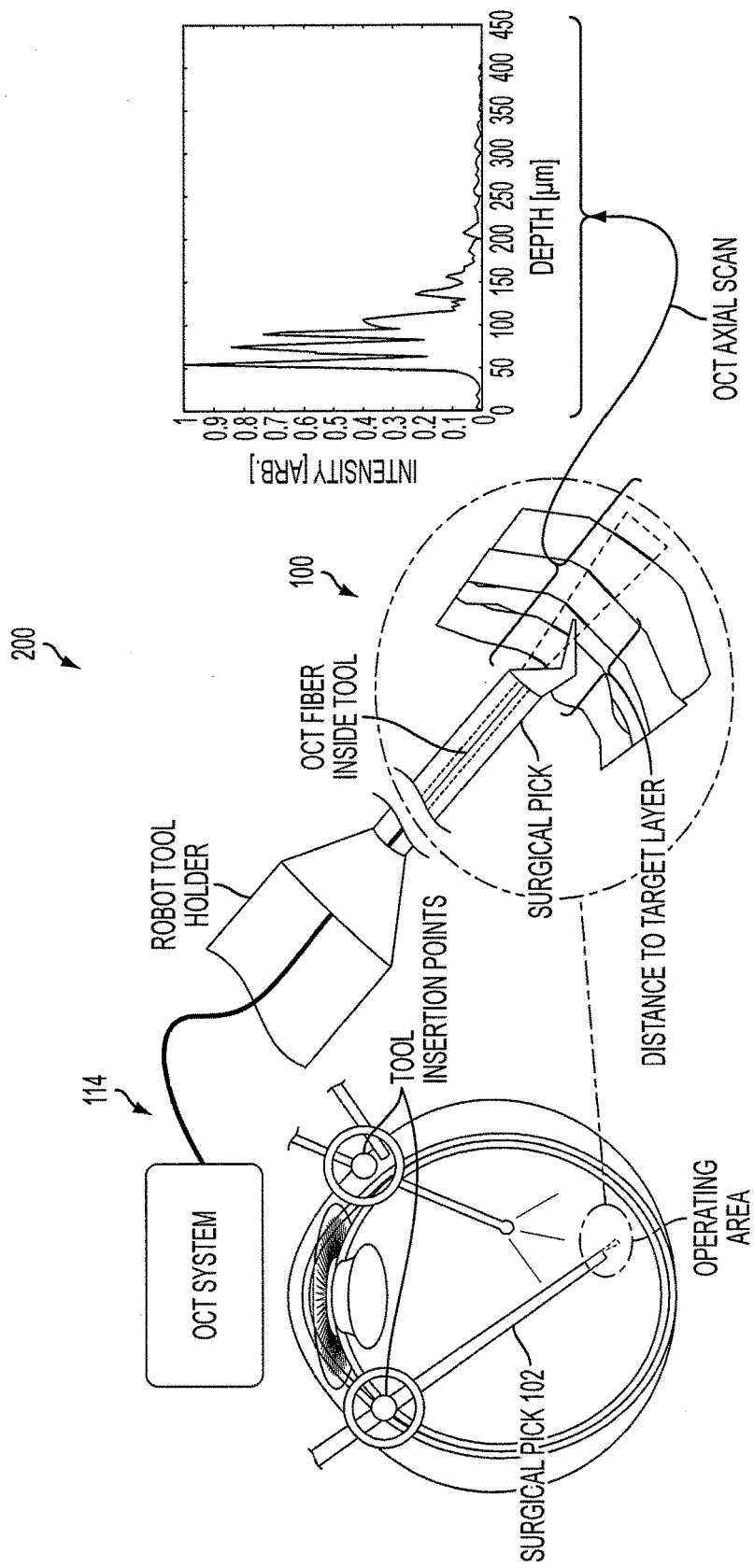
FIG. 5 provides a schematic illustration on the left of a surgical system according to an embodiment of the current invention. The right-hand side shows axial OCT scan data.
Figure 6:
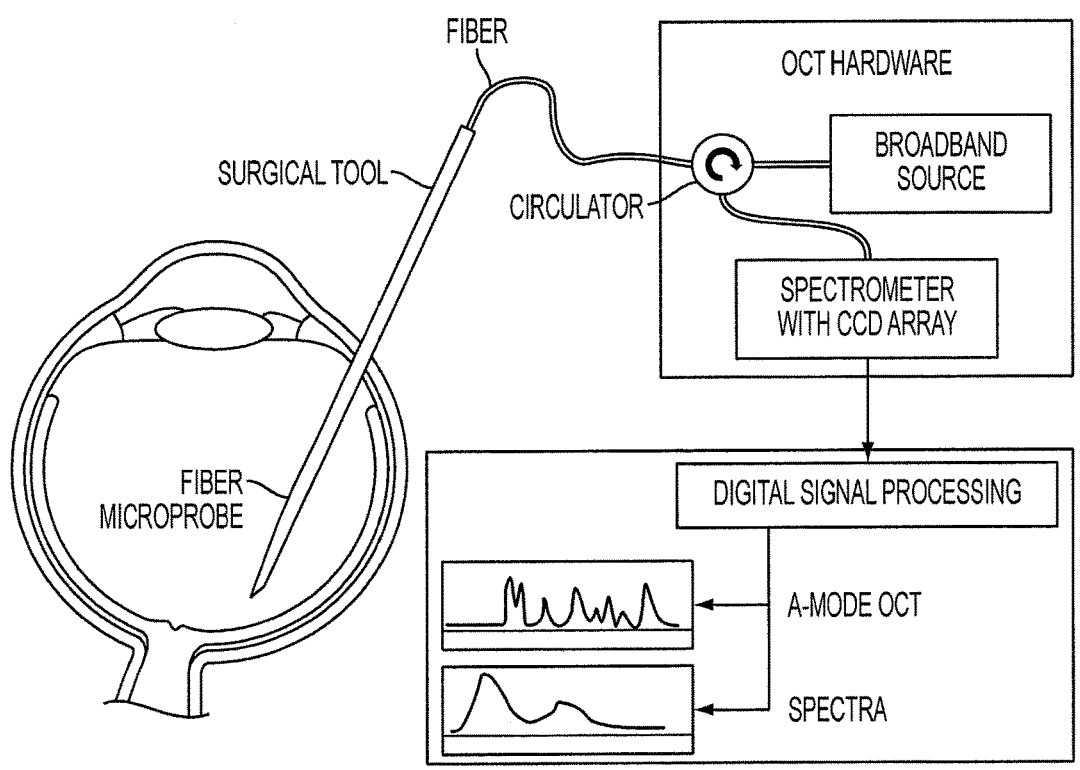
FIG. 6 is a schematic illustration of a surgical instrument according to an embodiment of the current invention.

In the example of FIG. 3, the surgical instrument 100 is shown with a portion of the optical sensor which can be connected through fiber coupler 110 to the remaining portion of the optical sensor. In the example of FIG. 5, the optical sensor 114 is an optical coherence tomography (OCT) system. In other embodiments, one could include more than one OCT or other type of optical sensor into the surgical instrument 100 within broad concepts of the current invention. In addition, although it can be advantageous for many applications to provide much of the optical sensor 114 external to the tool as is shown in the examples of FIGS. 3-5, the broad concepts of the current invention also include embodiments in which the entire sensor or sensors are included within the surgical tool. The optical coherence tomography system in the embodiment of FIG. 5 includes a single-mode optical fiber that provides the fixed end 116 of the optical sensor 114, the single-mode optical fiber being arranged to direct light to both the reference portion 112 of the surgical tool 102 and the tissue 118 proximate or in contact with the distal end 106 of the surgical tool 102 and to detect light reflected back from both the reference portion 112 of the surgical tool 102 and the tissue 118 to provide information regarding a relative distance of the distal end 106 of the surgical tool 102 to selected portions of the tissue 118. The term "reflected back" is intended to have a broad meaning to include both specular reflection as well as scattering, etc., as long as the light is reflected back. In addition, the term "light" is intended to have a broad meaning to include both visible light and light that is not visible to humans, such as infrared (IR) and ultraviolet light. In some embodiments of the current invention, the OCT system can make use of IR sources to provide significantly greater penetration depths into tissue than visible light, for example. Some embodiments of the current invention can include a broad band source in the OCT system, for example (see FIG. 6). However, the general concepts of the current invention are not limited to the particular types of light sources used in the optical sensor 114. Frequency domain OCT detection systems have been found to be suitable for some particular applications of the current invention; however, the general concepts of the current invention do not exclude the use of time domain OCT systems. Furthermore, some embodiments of the optical sensor can be without light sources, depending instead on ambient or external light sources.

Figure 7:
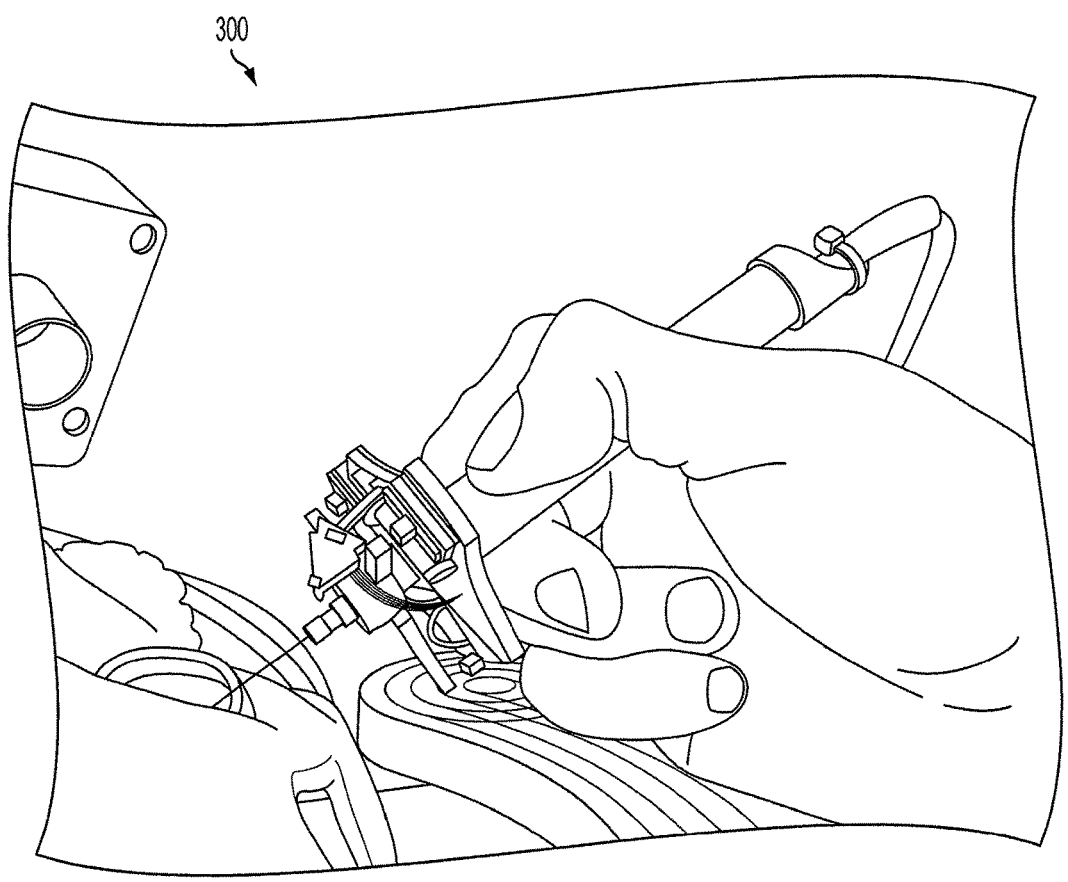
FIG. 7 shows a surgical system including a surgical instrument and a hand-held robot according to an embodiment of the current invention.

Alternatively, or in addition to the OCT system illustrated as the optical sensor 114, the optical sensor 114 could be or include a visual imaging system. For example, the optical imaging system could include an optical fiber, or a bundle of optical fibers to simultaneously image the reference portion 112 of the surgical tool 102 and the tissue 118 proximate or in contact with the distal end 106 of the surgical tool 102. In some embodiments, the surgical tool 102 can be a pick, for example, that is suitable for use in eye surgery. However, the general concepts of the current invention are not limited to the particular type of surgical tool. One can imagine a vast range of types of surgical tools that are suitable for surgical tool 102, such as, but not limited to picks, tweezers, knives, light delivery devices, scissors, injectors, vitrectomy tools, or other microsurgery tools. The surgical instrument can be adapted to integrate into a robotic system, such as is illustrated by surgical system 200 in FIG. 5 or the hand-held robot 300 shown in FIG. 7. In an embodiment of the current invention, a laser light projected on the tissue can be used to facilitate visual tracking or improve user interactivity. In some embodiments, the position of the sensor relative to the body of the tool is known so the sensor position can be tracked via tool tracking.

Figure 8:
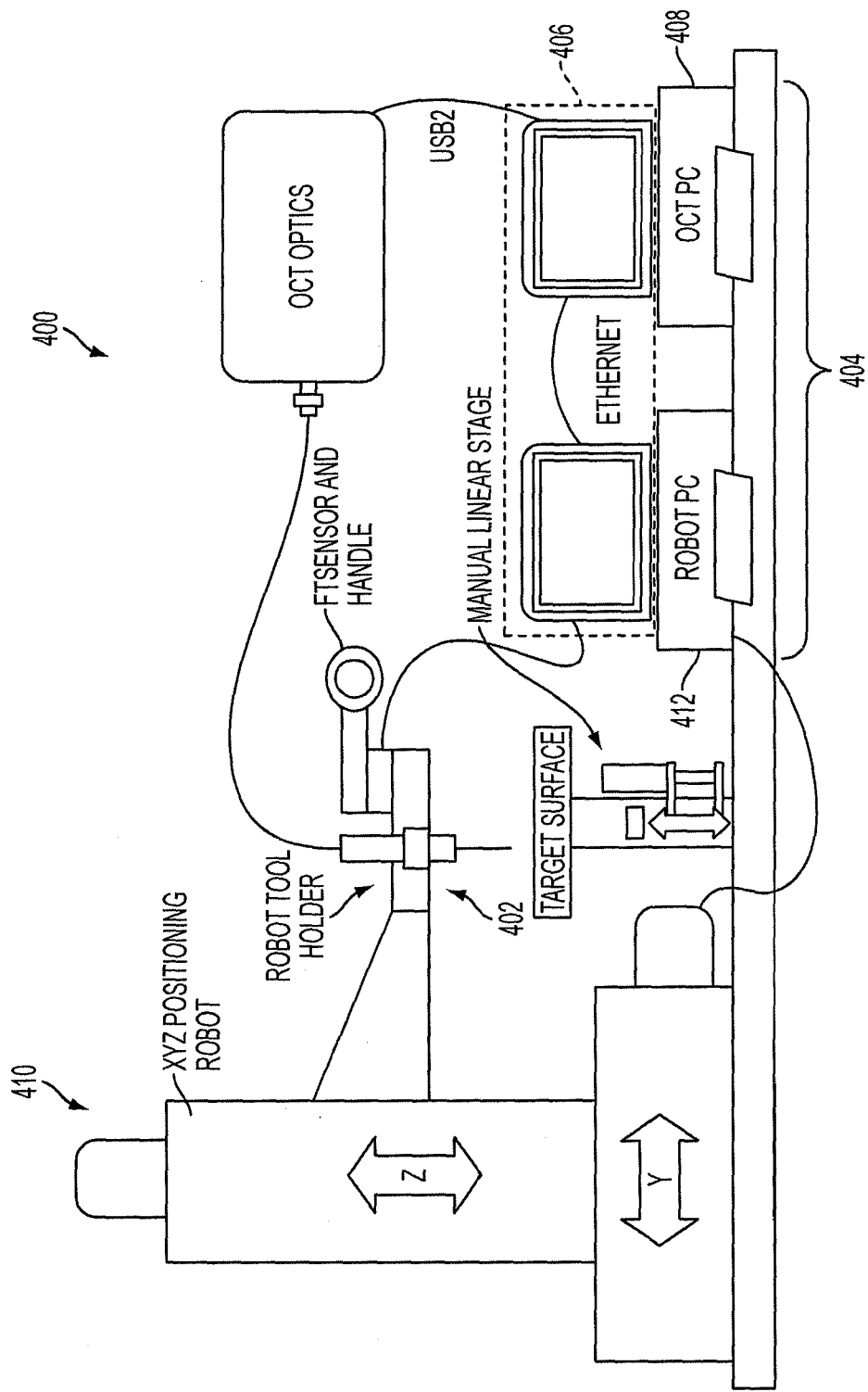
FIG. 8 is a schematic illustration of a surgical system according to an embodiment of the current invention.

FIG. 8 is a schematic illustration of a surgical system 400 that can include a visual tracking and annotation system according to an embodiment of the current invention. The surgical system 400 includes a surgical instrument 402, a data processor 404 in communication with the surgical instrument 402, and a display system 406 in communication with the data processor 404 and arranged to display information to a surgeon during a surgical procedure. According to some embodiments of the current invention, the surgical instrument 402 can be surgical instrument 100 as described above, for example. In the example of FIG. 8, the surgical instrument 402 has a dedicated data processor, such as OCT PC 408. However, the broad concepts of the current invention are not limited to only the particular architecture shown in FIG. 8. For example data processor could perform the processing for the OCT system as well as for other portions of the surgical system 400. The surgical system 400 also includes a robotic system 410. The robotic system 410 can have a dedicated data processor 412, for example, or it could be included on a single multipurpose processor along with the OCT processor, for example. The data processor 404 should be considered generally to cover one or more data processor, including one or more remote processors. The surgical system 400 illustrates video displays as an example of display system 406. However, the general concepts of the current invention are not limited to this particular example. The display could be, or include, head mounted displays, haptic or audio devices that serve the function of conveying information, and/or means of providing information to the surgeon. The robotic system 400 can be, but is not limited to, a steady-hand robotic system or a hand-held robotic system, for example. In some embodiments of the current invention, the data processor 404 can be configured to provide at least one of a warning signal or a feedback response signal based on a value of a relative position of the distal end of the surgical instrument to the tissue. In some embodiments of the current invention, the data processor 404 can be configured to provide a feedback response signal to the robotic system based on a value of at least one of a relative distance of the distal end of the surgical instrument from the tissue or a position of the instrument such that the robotic system provides a feedback response.

EXAMPLES

The following are a couple examples of the use of a visual tracking and annotation system according to some embodiments of the current invention. These examples are provided for illustration and are not intended to define the broad scope of the current invention.

VitroRetinal Surgery

The surgeon brings the OCT probe near an area of interest.

While a foot pedal is pressed (or voice command actuation) the surgeon sweeps the probe across an area of interest.

The location of the scan is tracked relative to the tissue and projected on the video feed via visual and/or external tool tracking. The time synchronized sensor data stream is associated with this path.

From this point on the tagged anatomical area is tracked and annotated accordingly.

The surgeon may choose to create another scan or investigate reexamine the existing ones.

The surgeon can request vocally to review "scan number 3" or hover over it with the surgical instrument.

The embodiments illustrated and discussed in this specification are intended only to teach those skilled in the art the best way known to the inventors to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A visual tracking and annotation system for surgical intervention in an eye, comprising:

a surgical instrument comprising a surgical tool suitable for use in the eye and an optical sensor attached to the surgical tool, wherein the surgical tool has a reference portion and the optical sensor has an end fixed relative to said reference portion such that light reflected by said reference portion can be detected by the optical sensor along with light reflected by tissue that is proximate to or in contact with a distal end of said surgical tool while in use in order to provide a distance of the distal end of the surgical tool to the tissue;

an image acquisition and display system arranged to obtain a plurality of image streams of a surgical region of interest and of said surgical instrument proximate to said surgical region of interest and to display said plurality of image streams to a user;

a tracking system configured to track a position of said surgical instrument relative to said surgical region of interest based on processing said plurality of image streams;

a data storage system in communication with said image acquisition and display system and said tracking system; and a data processing system in communication with said data storage system, said image acquisition and display system and said tracking system, wherein said data processing system is configured to generate an annotation from a first image of said plurality of image streams displayed to said user during said surgical intervention in response to an input signal from said user, the annotation being associated with the position of the surgical instrument and a location of the tissue relative to the surgical region of interest, wherein the data processing system is further configured to determine the location of the tissue based on the position of the surgical instrument and the distance of the distal end of the surgical tool to the tissue;

wherein the tracking system is further configured to acquire a location of the annotation relative to at least one corresponding anatomical landmark location acquired from said plurality of image streams, wherein said data storage system is configured to store said annotation and said location of said annotation relative to the corresponding anatomical landmark location, wherein said data processing system is further configured to retrieve said annotation and said location of said annotation relative to the corresponding anatomical landmark location from said data storage system, and wherein said data processing system is further configured to overlay said annotation onto a second image of said plurality of image streams having at least one of a different direction and position from said first image based on said location of said annotation relative to said corresponding anatomical landmark and processing of said first image.

2. A visual tracking and annotation system for surgical intervention according to claim 1, further comprising a user input device in communication with said data processing system to provide said input signal.

3. A visual tracking and annotation system for surgical intervention according to claim 2, wherein said user input device comprises at least one of a pedal, a keypad, a microphone, an eye tracking system and a switch.

4. A visual tracking and annotation system for surgical intervention according to claim 2, wherein said user input device comprises the surgical instrument.

5. A visual tracking and annotation system for surgical intervention according to claim 1, wherein said data processing system is further configured to annotate the first image displayed to said user to include at least one of a position or a track of said surgical instrument relative to said surgical region of interest.

6. A visual tracking and annotation system for surgical intervention according to claim 1, wherein said data processing system is further configured to retrieve information from said data storage system that corresponds to a position of said surgical instrument.

7. A visual tracking and annotation system for surgical intervention according to claim 1, wherein said surgical instrument comprises a sensor system comprising said optical sensor, said sensor system being constructed and arranged to collect data regarding localized portions of said surgical region of interest, and said surgical instrument being in communication with said data storage system such that data obtained by said surgical instrument can be saved for later retrieval.

8. A visual tracking and annotation system for surgical intervention according to claim 1, wherein said optical sensor comprises a visual imaging system.

9. A visual tracking and annotation system for surgical intervention according to claim 8, wherein said visual imaging system comprises an optical fiber, said visual imaging system being configured to simultaneously image said reference portion of said surgical tool and said tissue proximate or in contact with said distal end of said surgical tool.

10. A visual tracking and annotation system for surgical intervention according to claim 1, wherein said optical sensor comprises an optical coherence tomography system.

11. A visual tracking and annotation system for surgical intervention according to claim 10, wherein said optical coherence tomography system comprises an optical fiber that provides said fixed end of said optical sensor.

12. A visual tracking and annotation system for surgical intervention according to claim 11, wherein said surgical tool comprises a pick.

13. A visual tracking and annotation system for surgical intervention according to claim 12, wherein said distal end of said surgical tool is adapted to be held by a surgeon for performing manual surgery.

14. A visual tracking and annotation system for surgical intervention according to claim 12, wherein said distal end of said surgical tool is adapted to be attached to a robotic system for at least one of robotic or robot-assisted surgery.

15. A visual tracking and annotation system for surgical intervention according to claim 11, wherein said surgical tool is at least one of a pick, tweezers, a knife, a light delivery device, scissors, an injector, or a vitrectomy tool.

16. A visual tracking and annotation system for surgical intervention according to claim 1, wherein said surgical instrument comprises a sensor system comprising said optical sensor.

17. A visual tracking and annotation system for surgical intervention according to claim 1, wherein said surgical instrument is a user input device that is in communication with said data processing system to provide said input signal.

18. A visual tracking and annotation method for surgical intervention in an eye, comprising:

acquiring a plurality of images of a surgical region of interest and of a surgical instrument proximate to said surgical region of interest, wherein the surgical instrument comprises a surgical tool suitable for use in an eye and an optical sensor attached to the surgical tool, and wherein the surgical tool has a reference portion and the optical sensor has an end fixed relative to said reference portion such that light reflected by said reference portion can be detected by the optical sensor along with light reflected by tissue that is proximate to or in contact with a distal end of said surgical tool while in use in order to provide a distance of the distal end of the surgical tool to the tissue;

tracking a position of said surgical instrument relative to said surgical region of interest based on processing said plurality of said images;

generating an annotation from a first image of said plurality of images during said surgical intervention in response to an input signal from a user, wherein the annotation is associated with the position of the surgical instrument and a location of the tissue relative to the surgical region of interest, the location of the tissue being based on the position of the surgical instrument and the distance of the distal end of the surgical tool to the tissue;

acquiring and storing a location of said annotation relative to at least one corresponding anatomic landmark location from said plurality of images;

retrieving said annotation and said location of said annotation relative to the corresponding anatomical landmark location; and overlaying said annotation onto a second image of said plurality of images having at least one of a different direction and position from said first image based on said location of said annotation relative to the corresponding anatomical landmark location and processing of said first image.

19. A visual tracking and annotation method for surgical intervention according to claim 18, wherein said annotation includes at least one of a position or a track of said surgical instrument.

20. A visual tracking and annotation method for surgical intervention according to claim 18, wherein said annotation includes information retrieved from a data storage system that corresponds to a position of said surgical instrument.

21. A computer-readable medium comprising non-transient storage of software for visual tracking and annotation for surgical intervention, which when executed by a computer system, comprises:

processing a plurality of images of a surgical region of interest and of a surgical instrument proximate to said surgical region of interest, wherein the surgical instrument comprises a surgical tool suitable for use in an eye and an optical sensor attached to the surgical tool, and wherein the surgical tool has a reference portion and the optical sensor has an end fixed relative to said reference portion such that light reflected by said reference portion can be detected by the optical sensor along with light reflected by tissue that is proximate to or in contact with a distal end of said surgical tool while in use in order to provide a distance of the distal end of the surgical tool to the tissue;

processing tracking of a position of said surgical instrument relative to said surgical region of interest based on processing of said plurality of images;

processing an input signal from a user to generate an annotation from a first image of said plurality of images during said surgical intervention, wherein the annotation is associated with the position of the surgical instrument a location of the tissue relative to the surgical region of interest, the location of the tissue being based on the position of the surgical instrument and the distance of the distal end of the surgical tool to the tissue;

processing said annotation to store said annotation and a location of said annotation relative to at least one corresponding anatomical landmark location;

processing said annotation to retrieve said annotation and said location of said annotation relative to the corresponding anatomical landmark location; and processing said annotation to overlay said annotation onto a second image of said plurality of images having at least one of a different direction and position from said first image based on said location of said annotation relative to said corresponding anatomical landmark location and said first image.

22. A computer-readable medium according to claim 21, wherein said annotation includes at least one of a position or a track of said surgical instrument.

23. A computer-readable medium according to claim 21, wherein said annotation includes information retrieved from a data storage system that corresponds to a position of said surgical instrument.

* * * * *